United States Patent [19]

De Rooij et al.

[11] 4,021,422

[45] May 3, 1977

[54] PROCESS FOR THE RECOVERY OF ε-CAPROLACTAM FROM REACTION MIXTURE OF ε-CAPROLACTAM AND SULPHURIC ACID

[75] Inventors: Abraham H. De Rooij, Geleen; Jan Elmendorp, Brunssum, both of Netherlands

[73] Assignee: Stamicarbon B.V., Geleen, Netherlands

[22] Filed: Aug. 1, 1975

[21] Appl. No.: 601,018

[30] Foreign Application Priority Data

Aug. 5, 1974    Netherlands ..................... 7410450

[52] U.S. Cl. ........................................ 260/239.3 A
[51] Int. Cl.² ........................................ C07D 201/16
[58] Field of Search ........................... 260/239.3 A

[56] References Cited

UNITED STATES PATENTS

| | | | |
|---|---|---|---|
| 2,221,369 | 11/1940 | Cass | 260/239.3 A |
| 2,313,026 | 3/1943 | Schlack | 260/239.3 A |
| 2,605,261 | 7/1952 | Kahr | 260/239.3 A |
| 3,907,781 | 9/1975 | De Rooij et al. | 260/239.3 A |
| 3,937,789 | 2/1976 | Donati et al. | 260/239.3 A |

FOREIGN PATENTS OR APPLICATIONS

| | | | |
|---|---|---|---|
| 546,765 | 3/1974 | Switzerland | 260/239.3 A |
| 750,222 | 6/1956 | United Kingdom | 260/239.3 A |

*Primary Examiner*—Henry R. Jiles
*Assistant Examiner*—Robert T. Bond
*Attorney, Agent, or Firm*—Cushman, Darby & Cushman

[57] ABSTRACT

In commercial processes for producing epsilon-caprolactam, the caprolactam product is in admixture with sulfuric acid. An improved process for removing sulfuric acid from the caprolactam results from treating the admixture with ammonia at superatmospheric pressure.

6 Claims, 2 Drawing Figures

PROCESS FOR THE RECOVERY OF ε-CAPROLACTAM FROM REACTION MIXTURE OF ε-CAPROLACTAM AND SULPHURIC ACID

BACKGROUND OF THE INVENTION

The invention relates to a process for the recovery of ε-caprolactam from a reaction mixture of ε-caprolactam and sulphuric acid, in which the sulphuric acid is removed in the presence of water by reaction with ammonia.

Reaction mixtures containing ε-caprolactam and sulfuric acid result from the commercial process of preparing the lactam by the Beckmann rearrangement of cyclohexanone oxime to ε-caprolactam by treating the oxime with sulphuric acid, oleum or sulphur trioxide, as well as in the preparation of ε-caprolactam by reaction of cyclohexane-carboxylic acid, or a derivative thereof, with a nitrosating agent in the presence of sulphuric acid. To recover the caprolactam from said reaction mixture, the mixture may be treated with ammonia water in a neutralizer to form a supernatant lactam layer and a bottom layer consisting of a concentrated ammonium sulphate solution, after which the two layers are separated and processed as, for instance, in U.S. Pat. No. 2,605,261.

Alternatively, these reaction mixtures can be neutralized under pressure in the presence of ammonium sulphate crystals and a recycled ammonium sulfate-containing mother liquor; the mother liquor is the aforementioned bottom layer containing ammonium sulphate from which solid ammonium sulfate has been removed, as described in applicants' U.S. pat. application Ser. No. 482,601 now U.S. Pat. No. 3,907,781. The heat of neutralization released is utilized to convert water into steam.

Preferably, this conversion is effected at a pressure of between 1 and 2 atmospheres, because the use of a higher pressure would require a higher temperature and would result in higher lactam losses due to increased hydrolysis.

SUMMARY OF THE INVENTION

It has now been found that the neutralization under pressure, but in the absence of recycled ammonium sulphate-containing mother liquor and/or ammonium sulphate crystals, can be effected with a shorter residence time of the lactam in the neutralizer, so that at temperatures corresponding to the pressure range of over 2 atmospheres, e.g. 2-5 atmospheres, steam is produced and yet only slight losses due to hydrolysis of lactam result.

The process according to the invention has the following advantages over the known neutralization at atmospheric pressure:

a. The heat of neutralization can be removed without heat-exchanger.

b. The heat of neutralization is utilized to produce steam.

c. Better mixing is obtained owing to boiling phenomena, due to heat of neutralization, in the reaction mixture.

d. The removal of the heat of neutralization is effected at an almost constant temperature, which ensures a proper temperature control much more than when this heat is removed by cooling water and a heat exchanger, where crystals may deposit.

DETAILED DESCRIPTION OF THE INVENTION

The invention is directed to isolating ε-caprolactam from reaction mixtures containing ε-caprolactam and sulfuric acid. Typically, two processes known in the art for the production of ε-caprolactam result in mixtures of this product with sulfuric acid: (1) the Beckmann rearrangement of cyclohexanone oxime with sulfuric acid and (2) the reaction of cyclohexane carboxylic acid and a nitrosating agent in sulfuric acid.

The process according to the invention for the recovery of ε-caprolactam from a reaction mixture of ε-caprolactam and sulphuric acid, in which the sulphuric acid is neutralized by means of ammonia in the presence of water, is characterized in that (1) the neutralization is effected under superatmospheric pressure, i.e., at pressures exceeding one atmosphere, in the absence of ammonium sulphate crystals and/or recycled mother liquor containing ammonium sulphate; (2) the heat of neutralization is removed by evaporation of water to form steam; and (3) the neutralized mixture is separated into a lactam layer and an aqueous ammonium sulphate layer.

The advantage of the process over the process disclosed in applicants' aforementioned non-prepublished application, carried out at superatmospheric pressure, is that neutralization of the acidic reaction mixture in this manner cuts down on the residence time of the lactam in the neutralizer, so that the heat of neutralization can be removed at a higher temperature with formation of steam of a higher pressure and yet only slight losses due to hydrolysis of lactam result.

Ammonia is preferably added in the gaseous form. Addition of ammonia as aqueous ammonia with a concentration of e.g. 20-25 % by weight is also possible. Addition of ammonia results in boiling of the reaction mixture, due to the heat of neutralization resulting from the reaction of ammonia with sulphuric acid. Usually the reaction mixture to be neutralized contains about 1.3-1.7 moles of sulphuric acid per mole of lactam.

The process according to the invention may be effected at various superatmospheric pressures. As the pressure increases, steam of a higher pressure results. Steam of a higher pressure e.g. 2-5 atmospheres is of course more valuable than steam of a lower pressure, e.g. 1-2 atmospheres. However, at superatmospheric pressures exceeding 10 atmospheres, lactam losses owing to hydrolysis increase. Up to a pressure of about 10 atmospheres, these losses are not significant. A pressure exceeding 2 atmospheres and up to 5 atmospheres is found to be most suitable in practice of the process of the invention.

The aqueous ammonium sulphate layer and the lactam layer that are obtained in the process according to the invention may be processed in a known way.

According to the invention, the resulting aqueous ammonium sulphate layer can be processed in a particularly suitable way by adding this layer, if so desired after heat exchange with the water required for the formation of steam, to a new bath of reaction mixture of lactam and sulphuric acid. Lactam and ammonium sulphate can be recovered from the resulting reaction mixture by neutralization of the sulphuric acid with ammonia in the presence of a recycling amount of ammonium sulphate solution; simultaneous formation of ammonium sulphate crystals results. This subsequent processing may be undertaken at a lower pressure than that at which the neutralization of the original amount of reaction mixture of lactam and sulphuric acid is effected, preferably at atmospheric pressure, with dissipation of the heat of neutralization by evaporation of water from the solution. If the aqueous ammonium sulphate layer obtained in the neutralization of the original amount of reaction mixture of lactam and sulphuric acid is so processed, no separate crystallization equipment is required.

Alternatively, according to the invention, the aqueous ammonium sulphate layer can also be processed by adding this layer to a new batch of reaction mixture of lactam and sulphuric acid; then subjecting the resulting reaction mixture to an extraction with a solvent, e.g. chloroform or another chlorinated hydrocarbon as 1,2-dichloorethane or 1,1-2,2-tetrachloorethane, to form an aqueous layer and a solution of lactam in the extraction agent, and recovering the lactam from this solution. This processing method offers the advantage that the ammonium sulphate formed in the neutralization of the original amount of reaction mixture of lactam and sulphuric acid can be used in the recovery of lactam from the new batch of reaction mixture of lactam and sulphuric acid to form an aqueous solution containing ammonium hydrogensulphate, and, consequently, that ammonium sulphate is not produced, in the presence of the lactam. The resulting solution containing ammonium hydrogenslphate may, for instance, be burnt to produce sulphur dioxide. In this processing method, the lactam layer obtained from the original amount of reaction mixture of lactam and sulphuric acid may, if so desired, be added to the mixture to be extracted.

The process according to the invention will be explained further by the drawings attached hereto, in which two embodiments of the invention are shown diagrammatically.

Figure 1:
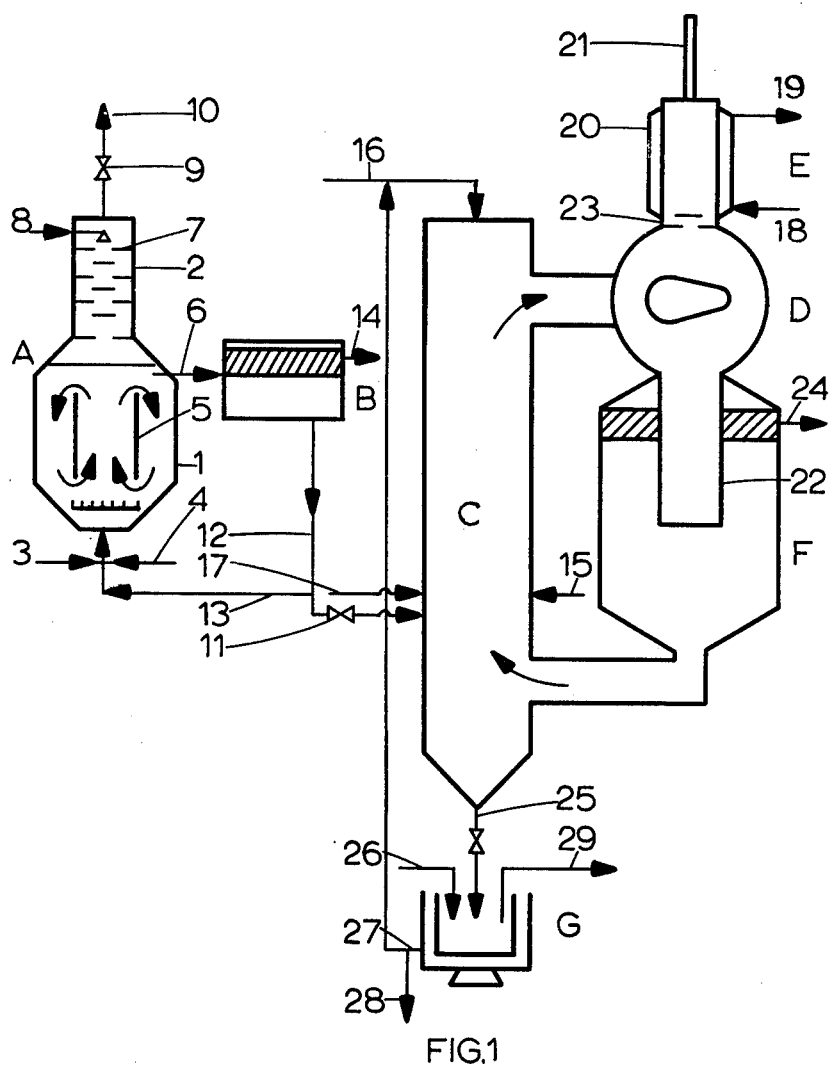
FIG. 1 shows the embodiment of the process in which the resulting ammonium sulphate layer is added to a batch of reaction mixture of lactam and sulphuric acid, and lactam and solid ammonium sulphate are recovered from the mixture at low pressure.

The references in FIG. 1 denote:
A: a first neutralizing reactor
B: a separator
C: a second neutralizing reactor
D: a boiling vessel
E: a condenser
F: a settling tank
G: a centrifuge The first neutralizing reactor A consists of a neutralizer 1 and a washing section 2. The top of the second neutralizing reactor C communicates through a side connection with the spherical boiling vessel D, into which the side connection debouches tangentially. A condenser E provided with a cooling jacket 20 is fitted on top of boiling vessel D. Boiling vessel D debouches at the bottom into settling tank F through a dip pipe 22. The settling tank, in turn, communicates with the lower end of the second neutralizing reactor C. When the apparatus is in operation, neutralizer 1, which is operated under superatmospheric pressure, is fed with a mixture of lactam and sulphuric acid through conduit 3 and with ammonia through conduit 4. A mixture of lactam and ammonium sulphate solution is passed from the reactor through conduit 6 into separator B.

If so desired, a guide cylinder 5 may be fitted in the neutralizer 1 to effect the best possible mixing in the reactor. To this end it is also possible to recycle, through conduit 13, part of the ammonium sulphate solution that is obtained as the bottom layer in separator B and which is passed to the second neutralizing reactor through a conduit 12 provided with an expansion valve 11. The steam produced in the neutralizer by the reaction heat released is recovered by way of the washing section 2 provided with plates 7 and through conduit 10 provided with a valve 9. In order to wash out any lactam and ammonia entrained by the steam, the required water is passed into the top of the washing section 2 through conduit 8.

The neutralized mixture flows through conduit 6 to separator B, where two layers are formed, a supernatant lactam layer and a bottom layer consisting of ammonium sulphate solution.

The lactam layer is discharged as the product through conduit 14. The ammonium sulphate solution is fed to a second neutralizing reactor C through conduit 12. This reactor is also fed with a second batch of rearrangement mixture through conduit 17, with ammonia through conduit 15, and, if so desired, with water through conduit 16. The second neutralizing reactor C is operated at a lower pressure than reactor A, e.g. at atmospheric pressure.

The boiling mixture, a suspension of ammonium sulphate crystals in a lactam solution saturated with ammonium sulphate, flows by way of boiling vessel D and settling tank F back into the lower end of neutralizing reactor C. The strongly acid feed is considerably diluted by this recycling liquid mass, which eliminates the risk of the acid concentration being too high in places, which would give rise to hydrolysis of lactam.

In the laboratory apparatus shown, the recycle flow is maintained by feeding in nitrogen along with the $NH_3$ gas through conduit 15, so that rising air bubbles produce the desired circulation. In embodiments on an industrial scale the recycle flow may be maintained by means of a pump.

Part of the water vapor produced in boiling vessel D is discharged through condenser E and conduit 21. The required cooling of condenser E is obtained by means of a cooler 20, to which cooling water is fed through conduit 18 and from which cooling water is discharged through conduit 19. If so desired, water may also be fed to the system through conduit 21. Some plates 23 are fitted in the lower end of condenser E to wash out lactam entrained by the water vapor.

In settling tank F, the space between the wall and the outside of dip pipe 22 is used as settling space; here a top layer of 'lactam oil' separates out, which is discharged through conduit 24.

A crystal suspension is discharged through conduit 25 to a centrifuge G, to which washing water is fed through conduit 26. Mother liquid and washing water are recycled through conduit 27; part of the recycle flow is periodically vented through conduit 28. Washed ammonium sulphate crystals are discharged as product through conduit 29.

Figure 2:
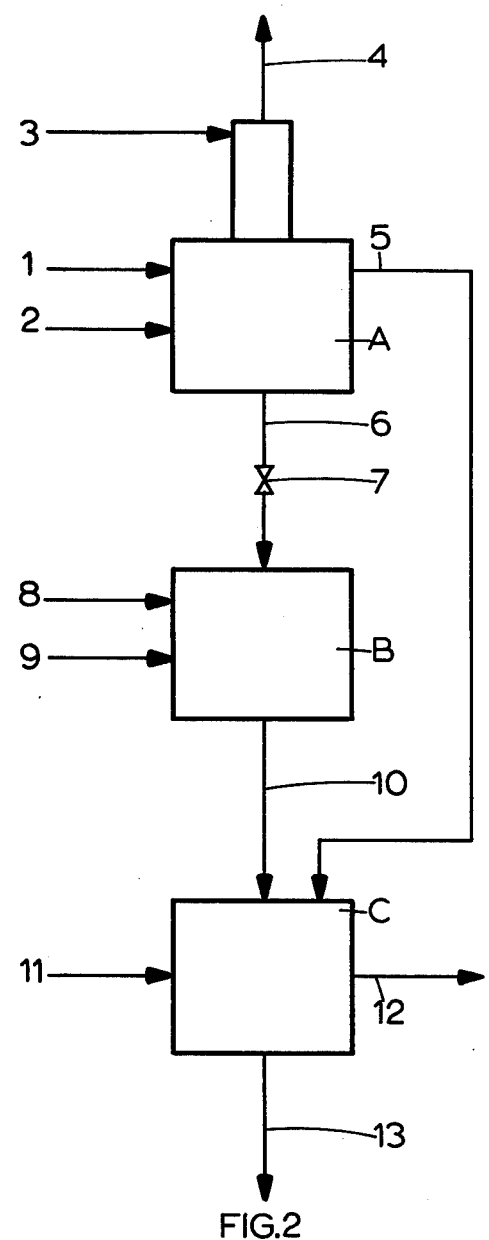
FIG. 2 shows a diagram of the embodiment of the process in which the ammonium sulphate layer is used to lower the acidity of another batch of rearrangement mixture.

FIG. 2 shows a diagram of a process in which the resulting ammonium sulphate layer is used to lower the acidity of a second batch of rearrangement mixture and the resulting mixture is subjected to an extraction. In this Figure A denotes a neutralizing device operating at superatmospheric pressure, B a diluting vessel operating at atmospheric pressure, and C an extraction device. Pressure-neutralizer A is fed with a mixture of lactam and sulphuric acid through conduit 1 and with ammonia through conduit 2. The steam produced is discharged through conduit 4, after entrained lactam and ammonia have been washed out of it by feeding in water through conduit 3. The lactam formed is discharged through conduit 5, and the ammonium sulphate solution is passed through conduit 6 and expansion valve 7 into diluting vessel B, which is also fed with a new batch of mixture of lactam and sulphuric acid through conduit 8, and, if so desired, with water through conduit 9. The heat content of the ammonium sulphate solution can be used, for instance, to preheat the water fed in through conduit 3. The temperature in the diluting vessel is kept at about 30° C. The amounts of ammonium sulphate solution and rearrangement mixture of lactam and sulphuric acid that are fed to diluting vessel B are such that the molar ratio of ammonium sulphate to the sum of ammonium sulphate and sulphuric acid in the resulting mixture ranges between the limits 0.4:1 and 0.6:1. After being diluted in diluting vessel B, the mixture flows through conduit 10 to the extraction device C, which is fed with an organic solvent for lactam, e.g. chloroform, through conduit 11. If so desired, the lactam discharged from the neutralizing device A through conduit 5 may also be fed to the extraction device C. A solution of lactam in the organic solvent is discharged through conduit 12.

The lactam may be recovered from this solution in a known way. An aqueous solution of ammonium hydrogensulphate is withdrawn from the system through conduit 13. This solution may be processed in a known way, e.g. by conversion into solid ammonium sulphate by neutralization and crystallization. The ammonium hydrogensulphate in this solution may also be decomposed thermally to recover ammonia and sulphur trioxide, or combusted to form a mixture of nitrogen, sulphur dioxide and water vapor. The sulphur dioxide and sulphur trioxide formed in these processes can then be processed into sulphuric acid or oleum, which compounds can be used again in the preparation of lactam. $\epsilon$-caprolactam is a starting material for nylon-6.

EXAMPLE I

In an embodiment of the type shown diagrammatically in FIG. 1, rearrangement mixture consisting of 1 kg of $\epsilon$-caprolactam and 1.3 kg of sulphuric acid is fed, per hour, to the first neutralizing reactor A, which is operated at 150° C and 3.4 atmospheres, through conduit 3 and 0.45 kg of ammonia through conduit 4. 2.51 kg of water are fed in through conduit 8. The residence time of the lactam in neutralizing reactor A in about 20 minutes. Under these conditions less than 0.5% by weight of the lactam is hydrolysed. 0.86 kg of 3.4-atm steam is recovered per hour through conduit 10.

The second neutralizer C, which is operated at atmospheric pressure and 180° C, is fed per hour with 1.75 kg of ammonium sulphate and 1.43 kg of water through conduit 12, with 0.93 kg of lactam and 1.21 kg of sulphuric acid through conduit 17, and with 0.42 kg of ammonia through conduit 15. The amount of water fed to the system through conduits 16 and 26 amounts to 0.26 kg. 1.33 kg of water vapor escape through conduit 21. The vent flow 28 contains 0.1 kg of water and 0.1 kg of ammonium sulphate. The amount of ammonium sulphate crystals discharged through conduit 29 is 3.28 kg.

EXAMPLE II

The reactor A of the device according to FIG. 2, which is operated at 150° C and 3.4 atmospheres, is fed per hour with 1 kg of lactam and 1.3 kg of sulphuric acid through conduit 1, with 0.45 kg of ammonia through conduit 2, and with 2.51 kg of water through conduit 3. 0.86 kg of 3.4-atm steam is recovered through conduit 4.

A second batch of rearrangement mixture consisting of 1 kg of lactam and 1.3 kg of sulphuric acid is fed to diluting vessel B through conduit 8, and 1.75 kg of ammonium sulphate and 1.43 kg of water through conduit 6. The mixture is passed through conduit 10 to extraction device C, where the lactam is extracted with 3 kg of chloroform supplied through conduit 11. At ammonium bisulphate solution containing 3.05 kg of $NH_4HSO_4$ and 3.05 kg of water is discharged through conduit 13.

What is claimed is:

1. In a process for the recovery of $\epsilon$-caprolactam from a reaction mixture of $\epsilon$-caprolactam and sulphuric acid, in which the sulphuric acid is neutralized in the presence of water by adding ammonia to the reaction mixture, the improvement comprising effecting neutralization at pressures exceeding one atmosphere and up to 10 atmospheres in the absence of ammonium sulphate crystals and/or recycled mother liquor containing ammonium sulphate, with dissipation of the heat of neutralization by evaporation of water to form steam, and separating the neutralized mixture into a lactam layer and an aqueous ammonium sulphate layer.

2. Process according to claim 1, wherein said pressure is in a range from a pressure which exceeds 2 atmospheres up to a pressure of 5 atmospheres.

3. Process according to claim 1, wherein the resulting aqueous ammonium sulphate layer, in a subsequent step, is added to a second batch of reaction mixture of $\epsilon$-caprolactam and sulphuric acid, and the lactam and solid ammonium sulphate are recovered from the mixture thus obtained by adding ammonia to the mixture to neutralize the sulphuric acid at a lower pressure than that at which the neutralization of the original amount of reaction mixture of lactam and sulphuric acid is effected, and in the presence of a recycling amount of aqueous ammonium sulphate solution, with simultaneous formation of ammonium sulphate crystals, wherein the heat of neutralization is dissipated by evaporation of water from the solution.

4. Process according to claim 3, wherein the lower pressure is atmospheric pressure.

5. Process according to claim 1, wherein the resulting aqueous ammonium sulphate layer is added to a second batch of reaction mixture of $\epsilon$-caprolactam and sulphuric acid and the reaction mixture thus obtained is extracted with a solvent to form an aqueous layer and a solution of lactam in the extraction agent used, and the lactam is recovered from this solution.

6. Process according to claim 5, wherein the lactam layer obtained from the original amount of reaction mixture of lactam and sulphuric acid is added to the reaction mixture to be extracted.

* * * * *